United States Patent
Lisonbee et al.

(10) Patent No.: US 6,866,868 B1
(45) Date of Patent: Mar. 15, 2005

(54) COMPOSITIONS INCLUDING DIFFERENT TYPES OF TRANSFER FACTOR, METHODS FOR MAKING THE COMPOSITIONS, AND METHODS OF TREATMENT USING THE COMPOSITIONS

(75) Inventors: David Lisonbee, Sandy, UT (US); William J. Hennen, Springville, UT (US); F. Joseph Daugherty, Omaha, NE (US)

(73) Assignee: 4Life Research, LC, Sandy, UT (US)

(*) Notice: Subject to any disclaimer, the term of this patent is extended or adjusted under 35 U.S.C. 154(b) by 0 days.

(21) Appl. No.: 10/663,353

(22) Filed: Sep. 15, 2003

(51) Int. Cl.[7] .............................................. A61K 35/20
(52) U.S. Cl. ...................................... 424/535; 424/581
(58) Field of Search ................................ 424/535, 581

(56) References Cited

U.S. PATENT DOCUMENTS 4,816,563 A    3/1989    Wilson et al.
6,468,534 B1   10/2002   Hennen et al.
2002/0044942 A1  4/2002  Dopson

FOREIGN PATENT DOCUMENTS

| EP | 914831 | * | 5/1999 |
| EP | 930316 | * | 7/1999 |

* cited by examiner

Primary Examiner—Jean C. Witz
(74) Attorney, Agent, or Firm—TraskBritt, PC

(57) ABSTRACT

A composition for eliciting a T-cell mediated immune response in a subject includes transfer factor from at least two different types of source animals. For example, the composition may include mammalian transfer factor and nonmammalian transfer factor. An example of the composition includes a combination of a colostrum-derived product, which includes the mammalian transfer factor, and an egg-derived product, which includes the nonmammalian transfer factor. Additionally, the egg-derived product may be substantially free of fat. Methods for forming the composition and eliciting T-cell mediated immune responses in subjects that have been treated with the composition are also disclosed.

14 Claims, 1 Drawing Sheet

COMPOSITIONS INCLUDING DIFFERENT TYPES OF TRANSFER FACTOR, METHODS FOR MAKING THE COMPOSITIONS, AND METHODS OF TREATMENT USING THE COMPOSITIONS

BACKGROUND OF THE INVENTION

1. Field of the Invention

The present invention relates generally to compositions which include transfer factor and, more specifically, to compositions which include transfer factor from different types of source animals. The present invention also relates to methods for making compositions that include different types of transfer factor and to methods for eliciting or enhancing a T-cell mediated immune response by the immune system of a subject.

2. Background of Related Art

Many, deadly pathogens are passed to humans from the animal kingdom. For example, monkeys are the sources of the type I human immunodeficiency virus (HIV-I), which causes acquired immune deficiency syndrome (AIDS) and monkeypox, which is similar to smallpox; ground-dwelling mammals are believed to be the source of the Ebola virus; fruit bats and pigs are the source of the Nipah virus; the Hendra virus comes from horses; the virus responsible for the "Hong Kong Flu" originated in chickens; and wild birds, especially ducks, are the sources of many of the deadly influenza viruses. Many diseases also have animal reservoirs. By way of example, mice carry Hanta virus, rats carry the Black Plague, and deer carry Lyme disease.

The Immune System

The immune systems of vertebrates are equipped to recognize and defend the body from invading pathogenic organisms, such as parasites, bacteria, fungi, and viruses. Vertebrate immune systems typically include a cellular component and a noncellular component.

The cellular component of an immune system includes the so-called "lymphocytes," or white blood cells, of which there are several types. It is the cellular component of a mature immune system that typically mounts a primary, non-specific response to invading pathogens, as well as being involved in a secondary, specific response to pathogens.

In the primary, or initial, response to an infection by a pathogen, white blood cells that are known as phagocytes locate and attack the invading pathogens. Typically, a phagocyte will internalize, or "eat" a pathogen, then digest the pathogen. In addition, white blood cells produce and excrete chemicals in response to pathogenic infections that are intended to attack the pathogens or assist in directing the attack on pathogens.

Only if an infection by invading pathogens continues to elude the primary immune response is a specific, secondary immune response to the pathogen needed. As this secondary immune response is typically delayed, it is also known as "delayed-type hypersensitivity." A mammal, on its own, will typically not elicit a secondary immune response to a pathogen until about seven (7) to about fourteen (14) days after becoming infected with the pathogen. The secondary immune response is also referred to as an acquired immunity to specific pathogens. Pathogens have one or more characteristic proteins, which are referred to as "antigens." In a secondary immune response, white blood cells known as B lymphocytes, or "B-cells," and T lymphocytes, or "T-cells," "learn" to recognize one or more of the antigens of a pathogen. The B-cells and T-cells work together to generate proteins called "antibodies," which are specific for (e.g., configured to bind to or otherwise "recognize") one or more certain antigens on a pathogen.

The T-cells are primarily responsible for the secondary, or delayed-type hypersensitivity, immune response to a pathogen or antigenic agent. There are three types of T-cells: T-helper cells, T-suppressor cells, and antigen-specific T-cells, which are also referred to as cytotoxic (meaning "cell-killing") T-lymphocytes (CTLs), or T-killer cells or natural killer (NK) cells. The T-helper and T-suppressor cells, while not specific for certain antigens, perform conditioning functions (e.g., the inflammation that typically accompanies an infection) that assist in the removal of pathogens or antigenic agents from an infected host.

Antibodies, which make up only a part of the noncellular component of an immune system, recognize specific antigens and, thus, are said to be "antigen-specific." The generated antibodies then basically assist the white blood cells in locating and eliminating the pathogen from the body. Typically, once a white blood cell has generated an antibody against a pathogen, the white blood cell and all of its progenitors continue to produce the antibody. After an infection is eliminated, a small number of T-cells and B-cells that correspond to the recognized antigens are retained in a "resting" state. When the corresponding pathogenic or antigenic agents again infect the host, the "resting" T-cells and B-cells activate and, within about forty-eight (48) hours, induce a rapid immune response. By responding in this manner, the immune system mounts a secondary immune response to a pathogen, the immune system is said to have a "memory" for that pathogen.

Mammalian immune systems are also known to produce smaller proteins, known as "transfer factors," as part of a secondary immune response to infecting pathogens. Transfer factors are another noncellular part of a mammalian immune system. Antigen-specific transfer factors are believed to be structurally analogous to antibodies, but on a much smaller molecular scale. Both antigen-specific transfer factors and antibodies include antigen-specific sites. In addition, both transfer factors and antibodies include highly conserved regions that interact with receptor sites on their respective effector cells. In transfer factor and antibody molecules, a third, "linker," region connects the antigen-specific sites and the highly conserved regions.

The Role of Transfer Factor in the Immune System

Transfer factor is a low molecular weight isolate of lymphocytes. Narrowly, transfer factors may have specificity for single antigens. U.S. Pat. Nos. 5,840,700 and 5,470,835, both of which issued to Kirkpatrick et al. (hereinafter collectively referred to as "the Kirkpatrick Patents"), disclose the isolation of transfer factors that are specific for certain antigens. More broadly, "specific" transfer factors have been generated from cell cultures of monoclonal lymphocytes. Even if these transfer factors are generated against a single pathogen, they have specificity for a variety of antigenic sites of that pathogen. Thus, these transfer factors are said to be "pathogen-specific" rather than antigen-specific. Similarly, transfer factors that are obtained from a host that has been infected with a certain pathogen are pathogen-specific. Although such preparations are often referred to in the art as being "antigen-specific" due to their ability to elicit a secondary immune response when a particular antigen is present, transfer factors having different specificities may also be present in such preparations. Thus, even the so-called "antigen-specific," pathogen-specific transfer factor preparations may be specific for a variety of antigens.

Additionally, it is believed that antigen-specific and pathogen-specific transfer factors may cause a host to elicit a delayed-type hypersensitivity immune response to pathogens or antigens for which such transfer factor molecules are not specific. Transfer factor "draws" at least the non-specific T-cells, the T-inducer and the T-suppressor cells, to an infecting pathogen or antigenic agent to facilitate a secondary, or delayed-type hypersensitivity, immune response to the infecting pathogen or antigenic agent.

Typically, transfer factor includes an isolate of proteins having molecular weights of less than about 10,000 daltons (D) that have been obtained from immunologically active mammalian sources. It is known that transfer factor, when added either in vitro or in vivo to mammalian immune cell systems, improves or normalizes the response of the recipient mammalian immune system.

The immune systems of newborns have typically not developed, or "matured," enough to effectively defend the newborn from invading pathogens. Moreover, prior to birth, many mammals are protected from a wide range of pathogens by their mothers. Thus, many newborn mammals cannot immediately elicit a secondary response to a variety of pathogens. Rather, newborn mammals are typically given secondary immunity to pathogens by their mothers. One way in which mothers are known to boost the immune systems of newborns is by providing the newborn with a set of transfer factors. In mammals, transfer factor is provided by a mother to a newborn in colostrum, which is typically replaced by the mother's milk after a day or two. Transfer factor basically transfers the mother's acquired, specific (i.e., delayed-type hypersensitive) immunity to the newborn. This transferred immunity typically conditions the cells of the newborn's immune system to react against pathogens in an antigen-specific manner, as well as in an antigen- or pathogen-nonspecific fashion, until the newborn's immune system is able on its own to defend the newborn from pathogens. Thus, when transfer factor is present, the immune system of the newborn is conditioned to react to pathogens with a hypersensitive response, such as that which occurs with a typical delayed-type hypersensitivity response. Accordingly, transfer factor is said to "jump start" the responsiveness of immune systems to pathogens.

Much of the research involving transfer factor has been conducted in recent years. Currently, it is believed that transfer factor is a protein with a length of about forty-four (44) amino acids. Transfer factor typically has a molecular weight in the range of about 3,000 to about 5,000 Daltons (Da), or about 3 kDa to about 5 kDa, but it may be possible for transfer factor molecules to have molecular weights outside of this range. Transfer factor is also believed to include three functional fractions, each of which may include different types of transfer factor molecules: an inducer fraction; an immune suppressor fraction; and an antigen-specific fraction. Many in the art believe that transfer factor also includes a nucleoside portion, which could be connected to the protein molecule or separate therefrom, that may enhance the ability of transfer factor to cause a mammalian immune system to elicit a secondary immune response. The nucleoside portion may be part of the inducer or suppressor fractions of transfer factor.

The antigen-specific region of the antigen-specific transfer factors is believed to comprise about eight (8) to about twelve (12) amino acids. A second highly-conserved region of about ten (10) amino acids is thought to be a very high-affinity T-cell receptor binding region. The remaining amino acids may serve to link the two active regions or may have additional, as yet undiscovered properties. The antigen-specific region of a transfer factor molecule, which is analogous to the known antigen-specific structure of antibodies, but on a much smaller molecular weight scale, appears to be hyper-variable and is adapted to recognize a characteristic protein on one or more pathogens. The inducer and immune suppressor fractions are believed to impart transfer factor with its ability to condition the various cells of the immune system so that the cells are more fully responsive to the pathogenic stimuli in their environment.

Sources of Noncellular Immune System Components

Conventionally, transfer factor has been obtained from the colostrum of milk cows, such as by the method described in U.S. Pat. No. 4,816,563 to Wilson et al. (hereinafter "Wilson"). While milk cows typically produce large amounts of colostrum and, thus, large amounts of transfer factor over a relatively short period of time, milk cows only produce colostrum for about a day or a day-and-a-half every year. Thus, milk cows are neither a constant source of transfer factor nor an efficient source of transfer factor.

Transfer factor has also been obtained from a wide variety of other mammalian sources. For example, in researching transfer factor, mice have been used as a source for transfer factor. Antigens are typically introduced subcutaneously into mice, which are then sacrificed following a delayed-type hypersensitivity reaction to the antigens. Transfer factor is then obtained from spleen cells of the mice.

While different mechanisms are typically used to generate the production of antibodies, the original source for antibodies may also be mammalian. For example, monoclonal antibodies may be obtained by injecting a mouse, a rabbit, or another mammal with an antigen, obtaining antibody-producing cells from the mammal, then fusing the antibody-producing cells with immortalized cells to produce a hybridoma cell line, which will continue to produce the monoclonal antibodies throughout several generations of cells and, thus, for long periods of time.

Antibodies against mammalian pathogens have been obtained from a wide variety of sources, including mice, rabbits, pigs, cows, and other mammals. In addition, the pathogens that cause some human diseases, such as the common cold, are known to originate in birds. As it has become recognized that avian (i.e., bird) immune systems and mammalian immune systems are very similar, some researchers have turned to birds as a source for generating antibodies.

Avian antibodies that are specific for pathogens that infect mammals, or "mammalian pathogens," have been obtained by introducing antigens into eggs. Alternatively, antibodies may be present in eggs following exposure of the source animal to antigens, including antigens of mammalian pathogens. U.S. Pat. No. 5,080,895, issued to Tokoro on Jan. 14, 1992 (hereinafter "the '895 patent"), discloses a method that includes injecting hens with pathogens that cause intestinal infectious diseases in neonatal mammals. The hens then produce antibodies that are specific for these pathogens, which are present in eggs laid by the hens. The '895 patent discloses compositions that include these pathogen-specific antibodies and use thereof to treat and prevent intestinal diseases in neonatal piglets and calves. Treatment of pathogenic infections in mammals with avian antibodies may have undesirable results, however, since the immune systems of mammals may respond negatively to the large avian antibody molecules by eliciting an immune response to the antibodies themselves. Moreover, as mammalian immune systems do not recognize avian antibodies as useful for their abilities to recognize certain pathogens, or the specificities of avian antibodies for antigens of such pathogens, avian antibodies often do not elicit the desired immune responses in mammals.

It is also known that transfer factor may be obtained from eggs. U.S. Pat. No. 6,468,534 to Hennen et al. (hereinafter "Hennen") describes a process by which female chickens (i.e., hens) are exposed to one or more antigens, which results in the elicitation of an immune response, including a secondary immune response, by the chickens. As a result of the secondary immune response, transfer factor molecules are present in the eggs of the chicken. The eggs may then be processed to provide a product in which the transfer factor is present. Such a product may take the form of a freeze-dried, or lyophilized, egg powder, and may include all or part of the egg. The egg powder may then be incorporated directly into gelatin capsules or mixed with other substances, then introduced into gelatin capsules.

FIG. 2 schematically depicts capsulation equipment of a type that is currently useful for capsulating egg-derived avian transfer factor in the form of an egg powder. Capsulation equipment 20 includes a composition supply hopper 24, a feed station 28, and an auger 26 in communication between each composition supply hopper 24 and feed station 28. Auger 26 transports the whole egg powder from composition supply hopper 24 to feed station 28.

When auger 26 operates, it is heated to a temperature which exceeds the relatively low melting point of cholesterol, from egg yolk, in the whole egg powder. The warmed cholesterol is sticky, coating auger 26, the conduit in communication therewith, and feed station 28, thereby decreasing the efficiency with which capsulation equipment 20 operates. Consequently, capsulation equipment must be disassembled and cleaned periodically, which may take a considerable amount of time (e.g., up to about 8 hours), resulting in a significant decrease in the productivity of capsulation equipment 20 and, thus, the number of capsules that may be formed therewith. Thus, processing of whole egg powder to obtain a transfer factor-containing product is somewhat undesirable.

Additionally, compositions which are derived from products (e.g., eggs or colostrum) from a single source animal typically only include transfer factor molecules which have specificity to antigens to which the source animal has been exposed. The consequence of such limited exposure may be that the effectiveness of such transfer factor-containing compositions in preventing or treating certain types of infections or conditions is also limited.

Accordingly, there is a need for a composition which is useful for causing an immune system of a treated subject to elicit an immune response to a broader array of pathogens, as well as for a method for improving the efficiency and productivity with which capsulation and other composition-forming equipment operates.

SUMMARY OF THE INVENTION

The present invention includes a composition for eliciting a T-cell mediated immune response in a subject. The composition includes transfer factor from at least two different types of source animals. The term "type," as used herein with respect to source animals, describes the source animals from which transfer factor may be obtained and refers to source animals from different classes (e.g. mammals, birds, reptiles, amphibians, insects, etc.). The term "type," as used herein, also refers to source animals from different subclasses, orders (e.g., artiodactyls, primates, carnivores, etc.), families (bovine, hominids, felines, etc.), subfamilies, genuses (e.g., cattle, humans, domestic cats, etc.), and even species and subspecies. Use of the term "type" herein with respect to transfer factor denotes the type of source animal from which the transfer factor was obtained.

An exemplary embodiment of the composition includes transfer factor from both mammalian and nonmammalian source animals, which types of transfer factor are also referred to herein as "mammalian transfer factor" and "nonmammalian transfer factor," respectively. By way of non-limiting example, the mammalian transfer factor may be included in the composition as colostrum or a fraction or extract thereof, which are collectively referred to herein as "colostrum-derived products," or otherwise, as known in the art (e.g., as a leukocyte (white blood cell) extract, as a splenic ("from the spleen") extract, etc.). Also by way of example, the nonmammalian transfer factor of the exemplary composition may be obtained from an egg or a fraction or extract thereof, which are also referred to herein as "egg-derived products."

When a composition of the present invention includes a colostrum-derived product and an egg-derived product, both products may be included in the mixture in amounts (e.g., by weight, by volume, etc., of the total mixture) that are about equal, or more of one of the colostrum-derived product and the egg-derived product than the other.

In another aspect, the present invention includes a method for capsulating an egg-derived product which includes transfer factor. The inventive capsulation method includes mixing a substantially fat-free component, such as a colostrum-derived product, which may or may not include transfer factor, with the egg-derived product before or while the egg-derived product is being introduced into capsulation equipment.

Additionally, the present invention includes a method for reducing the cleaning frequency of capsulation equipment used for capsulating an egg-derived product. That method includes mixing a less fatty or substantially fat-free substance, such as a colostrum-derived product, with the egg-derived product before or during introduction of the egg-derived product into the capsulation equipment.

The present invention also includes methods for treating a subject. Treatment methods that incorporate teachings of the present invention include administration of a composition according to the present invention to a subject. As the composition includes transfer factor, administration of the composition to the subject will cause the subject's immune system to elicit a T-cell mediated immune response or will enhance a T-cell mediated immune response by the subject's immune system which is already underway.

Other features and advantages of the present invention will become apparent to those of ordinary skill in the art through consideration of the ensuing description, the accompanying drawings, and the appended claims.

BRIEF DESCRIPTION OF THE DRAWINGS

In the drawings, which depict exemplary embodiments of various aspects of the present invention.

DETAILED DESCRIPTION

Figure 1:
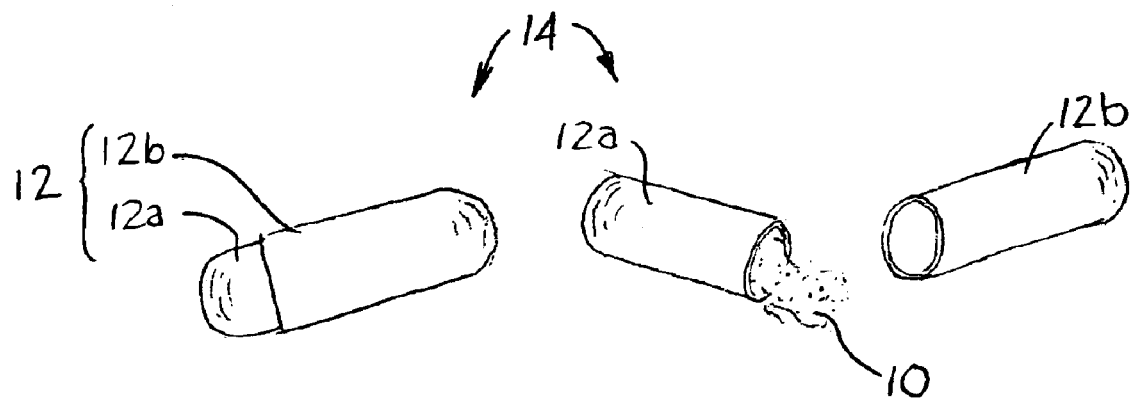
FIG. 1 depicts an example of the manner in which a composition that incorporates teachings of the present invention may be embodied.

An exemplary embodiment of composition that incorporates teachings of the present invention includes transfer factor from at least two different types of source animals. By way of nonlimiting example, a composition according to the present invention may include mammalian transfer factor and nonmammalian transfer factor.

The different types of transfer factor of the inventive composition may be obtained from any suitable source. For example, mammalian transfer factor may be obtained from colostrum, as described in Wilson, the disclosure of which is hereby incorporated herein in its entirety by this reference, or otherwise, as known in the art (e.g., a leukocyte (white blood cell) extract, a splenic (i.e., "from the spleen") extract, etc.). An exemplary source for nonmammalian transfer factor is an egg of an animal, such as a chicken, as described in Hennen, the disclosure of which is hereby incorporated herein in its entirety by this reference. Thus, a composition according to the present invention may include a first component which comprises a colostrum-derived product, as well as a second component that comprises an egg-derived product.

As compositions that incorporate teachings of the present invention include transfer factor from different types of source animals, they may include transfer molecules with a broader array of antigen-specificity or pathogen-specificity than conventional transfer factor-containing compositions. Thus, a composition according to the present invention is capable of enlisting the immune system of a treated animal to elicit a T-cell mediated immune response against a broader array of pathogens than those against which conventional transfer factor-containing compositions are effective. This is because different types of animals may be exposed to different types of antigens or pathogens, such as by vaccination, the animals' environments, or the like.

As an example, a composition which includes transfer factor-containing components from both cows and chickens will include transfer factor molecules which are specific to antigens or pathogens to which cows are exposed, as well as transfer factor molecules that have specificity for antigens or pathogens to which chickens are exposed. As both cows and chickens may be exposed to antigens or pathogens to which the other is not exposed, such a composition may include transfer factor molecules with antigen or pathogen specificities that would not be present in a composition that includes only transfer factor from cows (e.g., by way of a colostrum-derived product) or transfer factor from chickens (e.g., through an egg-derived product).

A composition of the present invention may include about the same amounts, measured in terms of weight or volume, of a colostrum-derived product and an egg-derived product (i.e., about 50% colostrum-derived product and about 50% egg-derived product). Alternatively, a composition that incorporates teachings of the present invention may include more colostrum-derived product (e.g., about 85% or 60%, by combined weight of the colostrum-derived product and egg-derived product) than egg-derived product (about 15% or 40%, by weight). As another alternative, the inventive composition may include more egg-derived product (e.g., about 60% or 85%, by weight) than colostrum-derived product (e.g., about 40% or 15% by weight). As another example, a composition that incorporates teachings of the present invention may include about one percent, by weight, of one of a colostrum-derived product and an egg-derived product and about 99%, by weight, of the other of the colostrum-derived product and the egg-derived product. Although specific amounts of colostrum-derived product and egg-derived product have been provided, any combination thereof is within the scope of the present invention.

In addition to including a source of transfer factor (e.g., a colostrum-derived product, an egg-derived product, etc.), a composition that incorporates teachings of the present invention may include one or more other ingredients, including, but not limited to, vitamins, minerals, proteins, natural products (e.g., herbs, mushrooms, roots, etc., or extracts thereof, and the like. Additional ingredients may be useful for providing further advantages to subjects to which the composition is administered, or may enhance the ability of the transfer factor in the composition to elicit or enhance a secondary, or delayed-type hypersensitivity, immune response.

As shown in FIG. 1, without limiting the scope of the present invention, a composition 10 according to the present invention may take the form of a powdered or particulate substance, which includes the multiple types of transfer factor (not shown). In order to ensure that an appropriate and precise dosage of composition 10 is administered to a subject (not shown), composition 10 may be contained within a gelatin capsule 12 of a type which is well-known and readily available to those in the art. The result is the illustrated capsule 14. Alternatively, a composition according to the present invention may be embodied as tablet, a so-called "caplet," an unencapsulated powder, a liquid, a gel, or in any other pharmaceutically acceptable form. Suitable processes for placing the inventive composition into any such form are readily apparent to those of skill in the art.

In an exemplary embodiment of a method for making or forming a composition according to the present invention, a first type of transfer factor may be combined with a second type of transfer factor. Additionally, one or more other types of transfer factor may be combined with the first and second types of transfer factor. The different types of transfer factor that are combined may be substantially purified transfer factor, components or "products" that include transfer factor, or any combination thereof.

Figure 2:
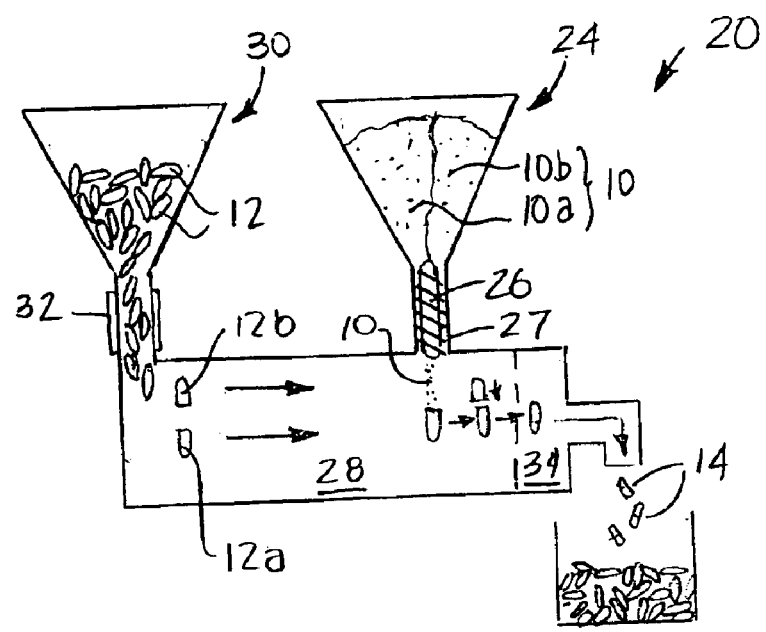
FIG. 2 is a schematic representation of capsulation equipment that may be used to introduce a powdered embodiment of the composition of the present invention into gelatin capsules.

Turning again to FIG. 2, a process for forming composition-filled capsules 14, such as that shown in FIG. 1, is provided merely as an example for a method for making a composition that incorporates teachings of the present invention. As illustrated, the composition 10 is made and composition-filled capsules 14 are formed using standard capsulation equipment 20 of a type known in the industry, such as the SF-135 capsule-filling machine available from CapPlus Technologies of Phoenix, Ariz.

In addition to one or more composition supply hoppers 24, an auger 26 associated with each composition supply hopper 24, and a feed station 28 with which each auger 26 and the conduit 27 within which auger 26 is contained communicates, capsulation equipment 20 includes one or more capsule hoppers 30, as well as a pneumatic feed system 32 for transporting capsule bodies 12a and/or caps 12b to feed station 28.

As the capsulation equipment will introduce the mixture into capsules, which may be swallowed by a subject, it is currently preferred that the substantially fat-free component and the egg-derived product be introduced into the capsulation equipment in powdered form. The substantially fat-free component dilutes the amount, or concentration, of fat (e.g., from egg yolk) present in the mixture relative to the concentration of fat which is present in the egg-derived product. Accordingly, the relative amounts of the substantially fat-free product and the egg-derived product may be tailored to provide a fat concentration that will minimize clogging of the capsulation equipment.

Continuing with the example of a composition 10 which includes a colostrum-derived product 10a as the substantially fat-free component and an egg-derived product 10b, colostrum-derived product 10a and egg-derived product 10b may be introduced simultaneously into a single composition supply hopper 24 of capsulation equipment 20. For example, colostrum-derived product 10a and egg-derived product 10b may be mixed upon introduction thereof into composition supply hopper 24, as shown, or premixed. By introducing a substance which has a lower fat content than egg-derived product 10b into composition supply hopper 24 along with egg-derived product 10b, the fat content (e.g., concentration) of the resulting mixture is less than that of egg-derived product 10b, reducing or eliminating the likelihood that composition supply hopper 24, auger 26, conduit 27, feed station 28, or any other component of capsulation equipment 20 will be coated with cholesterol or fat.

Following introduction of a predetermined amount of composition 10 into capsule bodies 12a at feed station 28, the filled capsule bodies 12a are transported to a capsule closing station 34, where capsule caps 12b are assembled therewith to fully contain composition 10 within capsule 12.

Again, a composition-filled capsule 14 is only one example of the manner in which a composition that incorporates teachings of the present invention may be embodied. The inventive composition may also take other forms, such as tablets, caplets, loose powder, liquid, gel, liquid-filled or gel-filled capsules, or any other pharmaceutically acceptable form known in the art, each of which may be made by known processes.

The composition of the present invention may be administered to a subject (e.g., a mammal, such as a human, a dog, or a cat, a bird, a reptile, a fish, etc.) by any suitable process (e.g., enterally, parenterally, etc.), depending, of course, upon the form thereof. For example, virtually any form of the composition (e.g., a capsule, tablet, caplet, powder, liquid, gel, etc.) may be administered orally (i.e., through the mouth of the subject), provided that the composition includes a pharmaceutically acceptable carrier of a type known in the art that will prevent degradation or destruction of transfer factor molecules by the conditions that persist in the digestive tract of the subject without substantially interfering with the efficacy of the transfer factor molecules included in the composition.

The dosage of composition or transfer factor within the composition that is administered to the subject may depend on a variety of factors, including, without limitation, the subject's weight, the health of the subject, or conditions (e.g., pathogens) to which the subject has been exposed.

Administration of the composition to the subject may cause the immune system of the subject to elicit a T-cell mediated immune response against one or more antigens or pathogens. Thus, the composition may be administered to a subject to treat a disease state that the subject is experiencing, to prevent the subject from exhibiting a disease state caused by a particular pathogen, or to merely enhance the overall health of the subject's immune system and abilities to fight off infecting or invading pathogens.

The following EXAMPLES illustrate the enhanced ability of a composition which includes transfer factor from multiple types of source animals to cause an immune system of a treated subject to elicit a T-cell mediated immune response to various types of pathogens, in the form of target cells. The target cells included bacteria (e.g., C. pneumoniae and H. pylori) and viruses (e.g., herpes simplex virus-1 (HSV-1) and herpes simplex virus-2 (HSV-2)) in the form of virally infected cells, as well as to cancerous, or malignant, cells (e.g., K562 erythroleukemic cells).

The in vitro technique that was used to make these determinations was the so-called "chromium-51 release assay," which includes measurement of the amount of radioactive chromium-51 (Cr-51) released by cells that have been attacked by NK cells. The radioactivity measurement may be obtained, for example, with a Beckman 2000 Gamma Counter, which is available from Beckman Coulter, Inc., of Fullerton, Calif.

In the EXAMPLES, a fixed amount (5 micrograms per milliliter of nutrient media and cellular milieu) of a powdered composition was provided in the nutrient media and cellular milieu, along with a substantially fixed amount of NK cells. Examples of the powdered compositions that were used include bleached wheat flour, Transfer Factor™ (TF), available from 4Life Research, LLC, of Sandy, Utah, Transfer Factor Plus™ (TFP), also available from 4Life Research, avian transfer factor available in a lyophilized (ie., freeze-dried) whole egg powder, and mixtures of TF and TFP (both the formula marketed in the United States and that marketed internationally) with avian transfer factor in a ratio of about 85% TF or TFP (ie., bovine transfer factor), by weight, to about 15% avian transfer factor, by weight. The powdered composition, nutrient media, NK cells, and target cells were mixed and incubated for four hours prior to measuring the radioactive atoms that were released by disruption of the target cells by the NK cells. Each exemplary reaction was conducted in triplicate, with the results of the three reactions having been averaged.

The following TABLE includes data of the counts per minute obtained with each combination of target cells and powdered composition, as well as the effectiveness of each powdered composition in eliciting an NK cell-mediated immune response against the target cells relative to the NK cell-mediated immune response relative to (measured in percent increase) the same types and concentrations of target cells in the presence of bleached wheat flour.

TABLE

| Composition | Target Cells | | | | |
|---|---|---|---|---|---|
| | C. Pneu | H. Pyl | K562 | HSV-1 | HSV-2 |
| Flour | 1323/ | 1121/ | 1267/ | 2017/ | 1262/ |
| TF | 2593/ | 2499/ | 2445/ | 2240/ | 2473/ |
| % increase | 196% | 223% | 193% | 110% | 196% |
| TFP | 3386/ | 2701/ | 3243/ | 2944/ | 1956/ |
| % increase | 256% | 241% | 256% | 146% | 155% |
| 100% Avian TF | 2553/ | 1860/ | 2483/ | 2985/ | 2183/ |
| % increase | 193% | 166% | 196% | 148% | 173% |
| Bov-Av TF | 14,857/ | 11,434/ | 6,639/ | 17,910/ | 10,626/ |
| % increase | 1123% | 1020% | 524% | 888% | 842% |
| Bov-Av TFP US | 61,956/ | 55,432/ | 40,075/ | 80,498/ | 46,933/ |
| % increase | 4683% | 4944% | 3163% | 3991% | 3719% |
| Bov-Av TFP Intl | 57,471/ | 47,855/ | 36,401/ | 73,660/ | 42,693/ |
| % increase | 4344% | 4267% | 2873% | 3652% | 3383% |

The results that are set forth in the TABLE show that administration of a composition of the present invention to a subject will likely increase the subject's secondary, or delayed-type hypersensitivity, immune response, as effected by NK cells, against one or more pathogens to a degree which far exceeds the NK cell activity initiated by both colostrum-derived transfer factor and egg-derived transfer factor alone. In fact, the results show that a composition that incorporates teachings of the present invention may result in facilitation of the activity of NK cells with an unexpected degree of synergy.

Although the foregoing description contains many specifics, these should not be construed as limiting the scope of the present invention, but merely as providing illustrations of some of the presently preferred embodiments. Similarly, other embodiments may be devised without departing from the spirit or scope of the present invention. Features from different embodiments may be employed in combination. The scope of the invention is, therefore, indicated and limited only by the appended claims and their legal equivalents rather than by the foregoing description. All additions, deletion and modifications to the invention as disclosed herein which fall within the meaning and scope of the claims are to be embraced thereby.

What is claimed:

1. A method for reducing the cleaning frequency of processing equipment used for capsulating an egg-derived product, comprising:

combining a colostrum-derived product with an egg-derived product before or during introduction of the egg-derived product into the capsulation equipment.

2. The method of claim 1, wherein said combining comprises combining about equal weights of said colostrum-derived product and the egg-derived product.

3. The method of claim 1, wherein said combining comprises combining said colostrum-derived product in a greater amount, by weight, than the egg-derived product with the egg-derived product.

4. The method of claim 1, wherein said combining comprises combining said colostrum-derived product, in a lesser amount, by weight, than the egg-derived product with the egg-derived product.

5. The method of claim 1, further comprising:
    defatting the egg-derived product.

6. The method of claim 1, further comprising:
    combining at least one vitamin with at least one of the egg-derived product and said colostrum-derived product.

7. The method of claim 1, wherein said combining comprises combining said colostrum-derived product and the egg-derived product with at least one of said colostrum-derived product and the egg-derived product including transfer factor.

8. A method for reducing the cleaning frequency of equipment used for processing an egg-derived product, comprising:

combining a colostrum-derived product with an egg-derived product before or during introduction of the egg-derived product into the equipment.

9. The method of claim 8, wherein said combining comprises combining about equal weights of said colostrum-derived product and the egg-derived product.

10. The method of claim 8, wherein said combining comprises combining said colostrum-derived product in a greater amount, by weight, than the egg-derived product with the egg-derived product.

11. The method of claim 8, wherein said combining comprises combining said colostrum-derived product, in a lesser amount, by weight, than the egg-derived product with the egg-derived product.

12. The method of claim 8, further comprising:
    defatting the egg-derived product.

13. The method of claim 8, further comprising:
    combining at least one vitamin with at least one of the egg-derived product and said colostrum-derived product.

14. The method of claim 8, wherein said combining comprises combining said colostrum-derived product and the egg-derived product with at least one of said colostrum-derived product and the egg-derived product including transfer factor.

* * * * *